(12) United States Patent
Han et al.

(10) Patent No.: US 6,234,005 B1
(45) Date of Patent: May 22, 2001

(54) PARTICLE ANALYZING SYSTEM FOR A CLEAN ROOM SMOCK AND METHOD OF ANALYZING PARTICLES

(75) Inventors: Youn-soo Han, Kyungki-do; Hyeug-ki Kim, Seoul; Hyun-joon Kim, Kyungki-do; Ho-wang Kim, Seoul, all of (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/206,236

(22) Filed: Dec. 7, 1998

(30) Foreign Application Priority Data

Dec. 24, 1997 (KR) .................................................. 97-73508

(51) Int. Cl.$^7$ ........................... G01N 15/02; G01N 15/08
(52) U.S. Cl. ............................................... 73/28.01; 73/38
(58) Field of Search ...................................... 73/28.01, 38

(56) References Cited

U.S. PATENT DOCUMENTS

| 4,885,930 | * | 12/1989 | Werner et al. ............................ 73/37 |
| 5,390,531 | * | 2/1995 | Taylor ..................................... 73/40 |
| 5,939,617 | * | 8/1999 | Lim et al. ................................. 73/38 |

FOREIGN PATENT DOCUMENTS

46740 * 3/1982 (EP) ...................................... 732/38

* cited by examiner

*Primary Examiner*—Daniel S. Larkin
(74) *Attorney, Agent, or Firm*—Jones Volentine, L.L.C.

(57) ABSTRACT

A particle analyzing system for a clean room smock includes a mannequin corresponding to the shape of a human body and having a clean room smock placed thereon. A gas supply apparatus is connected to the mannequin, and is operative to discharge a gas at a first set of sites on the mannequin. A particle supply apparatus is connected to the mannequin, and is operative to discharge particles at a second set of sites on the mannequin.

19 Claims, 2 Drawing Sheets

Fig.1

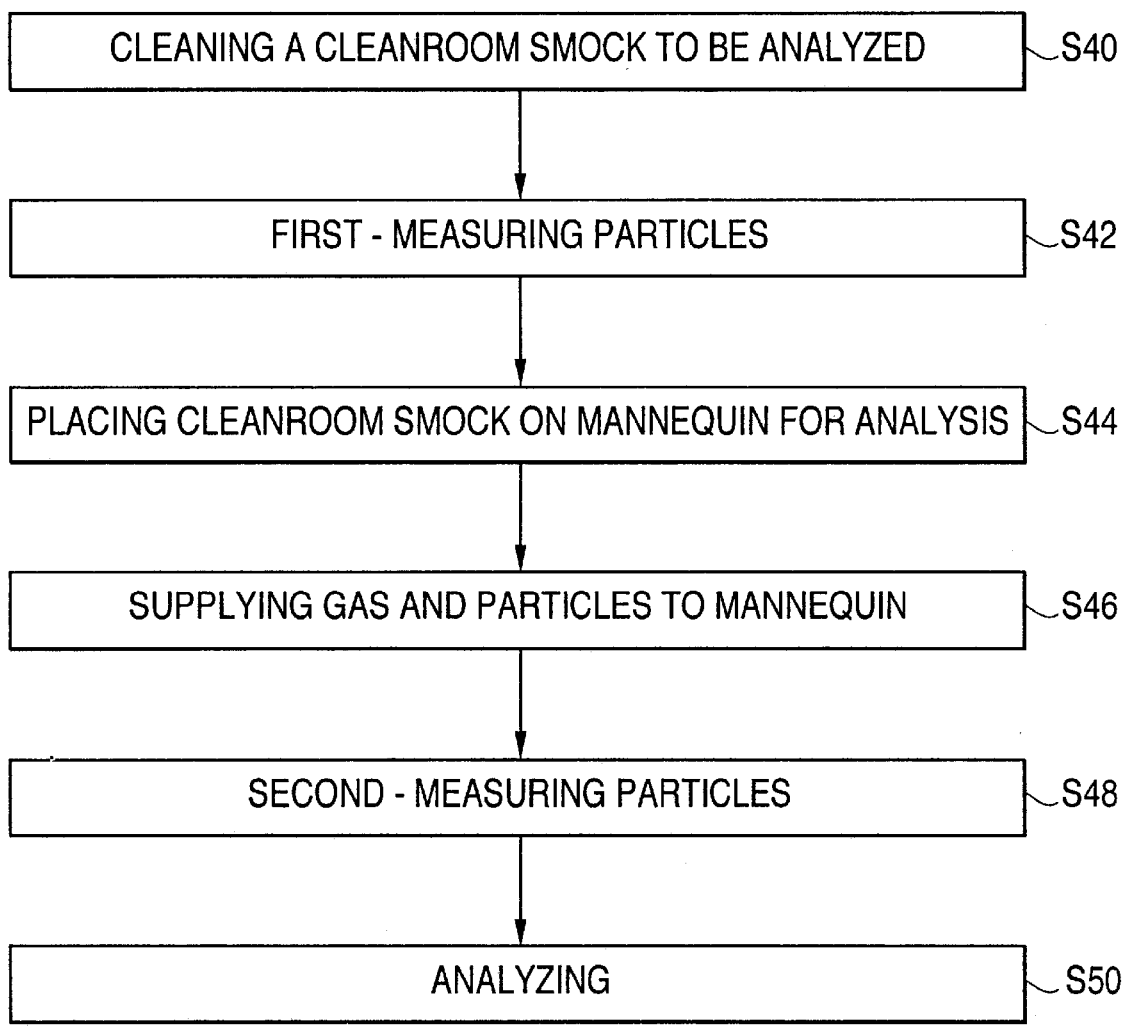

PARTICLE ANALYZING SYSTEM FOR A CLEAN ROOM SMOCK AND METHOD OF ANALYZING PARTICLES

BACKGROUND OF THE INVENTION

1. Field of the Invention

The present invention relates to a particle analyzing system for a clean room smock and a method of analyzing particles. More particularly, the present invention accurately measures the amount of the particles emanating from the clean room smock that is used in the semiconductor device fabrication process.

2. Description of the Related Art

Semiconductor device fabrication processes are generally performed within a highly-purified clean room because even very fine particles can contaminate the devices, thereby causing device malfunctions or inferior quality devices.

In order to reduce particle contamination generated by the manufacturing personnel, clean room operators and technicians wear a clean room smock covering their entire body, including headgear, mask, gloves, shoes, etc. The seams of the clean room smock are also specially manufactured to prevent particle generation as much as possible, and the seams are located on the back side of the smock. In addition, the clean room smock itself is made of a material which produces the least amount of particles as possible.

Despite such precautions, particles produced by the operators and the clean room smock itself still enter the clean room, and such contamination constitutes the main cause of device failure or malfunctions.

Efforts continue to try and improve the clean room smock itself, as well as employing test apparatus to measure and analyze the causes of particle generation. Such conventional test apparatus include a body box tester, a garment chamber, a Tumbler tester, and a Helmkedram tester.

In the body box tester, an operator wearing the clean room smock performs various fabrication processes inside a hexahedral box-shaped chamber for a certain time while the air stream within the chamber flows downward. The particles produced by the operator are collected, and the number of the particles having a size greater than a certain level is determined.

The garment chamber test is similar to the body box tester, with the added benefit that particles generated within the upper part of the chamber can be analyzed separately from those generated in the lower part of the chamber.

In the Tumbler tester and Helmkedram tester, a clean room smock is placed in a chamber and rotated for a certain period to pressurize or inflate the clean room smock. The particles generated by the clean room smock due to the pressurization are collected, and the number of the particles having a size greater than a certain level is determined.

Particle counters employing lasers are installed in each of the body box tester, the garment chamber, the Tumbler tester, and the Helmkedram tester so as to measure the number of the particles having a size greater than a certain level.

However, the particle measurement results from the body box tester and the garment chamber are usually different, with the measurements being dependent on, among other things, the personal cleanliness of the operator, the smoothness of the operator's movements inside the chamber, the kind of the clothes worn by the operator under the clean room smock, and the measurement time.

In addition, more particles are produced from certain parts of the operator's body such as the face, i.e. nose and mouth, compared with other parts of the body, but the body box tester and the garment chamber only measure an aggregate of particles collected, and cannot measure the number of particles produced from discrete parts of the body.

Further, the Tumbler tester and the Helmkedram tester only measure the number of the particles produced by the clean room smock itself, without consideration of the particles produced by an operator, so that the reliability of the measurement results is low and the measurement result varies according to the initial cleanliness of the clean room smock.

SUMMARY OF THE INVENTION

The present invention is directed to a particle analyzing system for a clean room smock, and a method of analyzing particles, which easily measures the number of the particles produced by the clean room smock itself, and excludes parameters attributable to an operator.

Another object of the present invention is to provide a particle analyzing system for a clean room smock, and a method of analyzing particles, that prevents different analysis results according to the conditions of the clean room smock itself, such as the cleanliness of the clean room smock and the material for the clean room smock.

A further object of the present invention is to provide a particle analyzing system for a clean room smock, and a method of analyzing particles, which measures the number of the particles produced from certain discrete parts of the clean room smock.

To achieve these and other advantages and in accordance with the purpose of the present invention, a particle analyzing system of a clean room smock used in a clean room includes a mannequin, corresponding to the shape of a human body, wearing a clean room smock, a gas supply apparatus attached to the mannequin that discharges a gas at certain sites along the mannequin; and a particle supply apparatus attached to the mannequin that discharges particles at other sites along the mannequin.

In another aspect, the present invention provides a method of analyzing particles of a clean room smock, including steps of cleaning a clean room smock to be analyzed; pressurizing the clean room smock to generate particles remaining on the clean room smock; measuring the number of particles generated by the clean room smock; placing the clean room smock on a mannequin corresponding to the shape of a human body; supplying a gas under pressure through a gas supply line to a first set of sites on the mannequin; supplying particles through a particle supply line to a second set of sites on the mannequin; and measuring the number of the particles discharged from the clean room smock. The method further includes analyzing the number of the particles discharged from the clean room smock.

It is to be understood that both the foregoing general description and the following detailed description are exemplary and explanatory and are intended to provide further explanation of the invention as claimed.

BRIEF DESCRIPTION OF THE DRAWINGS

In the accompanying drawings:

FIG. 1 illustrates a particle analyzing system for a clean room smock according to one embodiment of the present invention; and FIG. 2 illustrates one embodiment of a method of analyzing particles using the clean room smock of FIG. 1 according to the present invention.

DETAILED DESCRIPTION OF THE PREFERRED EMBODIMENTS

The present invention now will be described with reference to the accompanying drawings in which preferred embodiments of the invention are shown.

Figure 1:
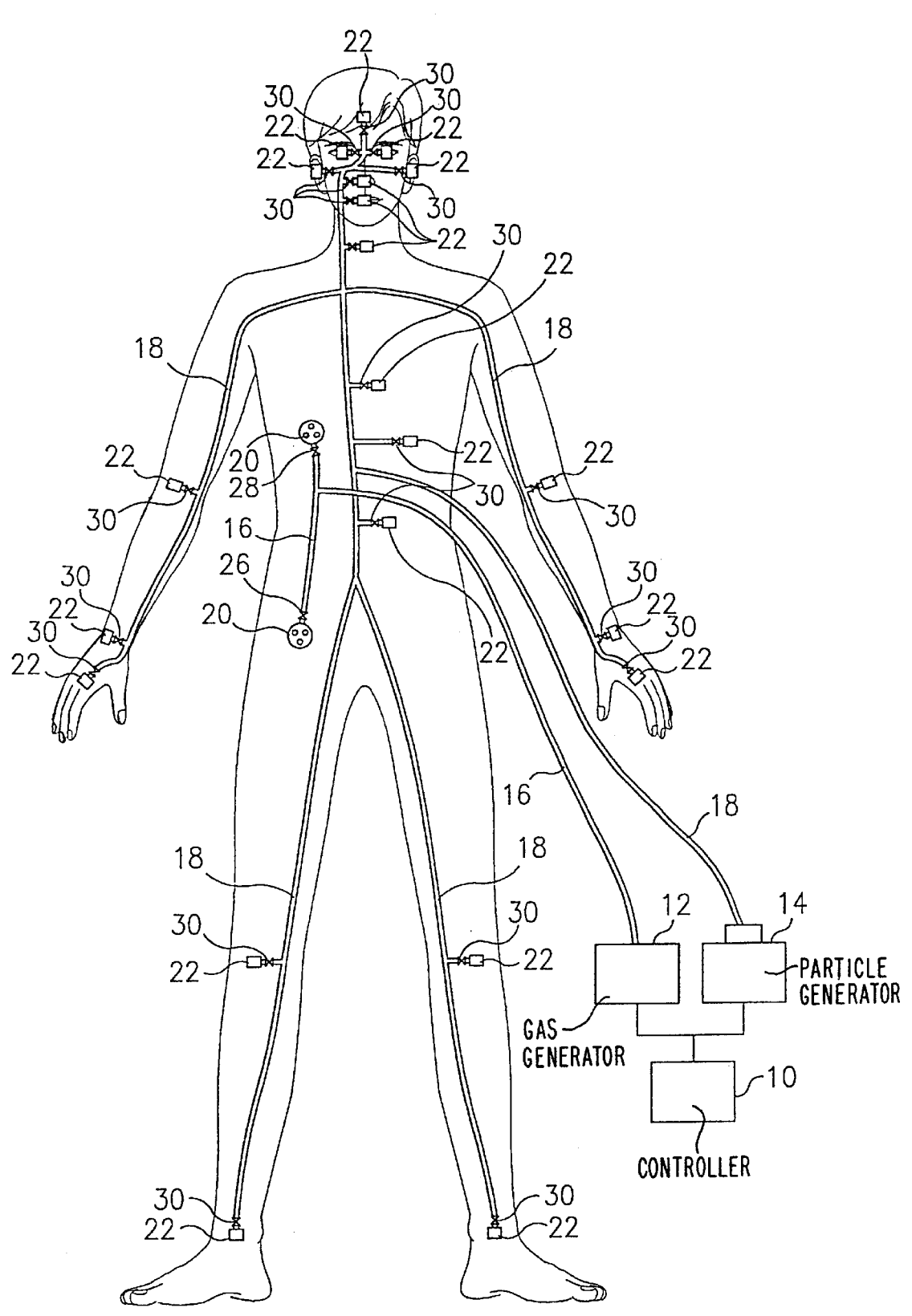

FIG. 1 illustrates a particle analyzing system for a clean room smock according to the present invention. The particle analyzing system generally includes a mannequin 5, which corresponds to the shape of the human body, and which is specially configured with gas and particle supply apparatus to test the particle generating attributes of a conventional clean room smock 6 that is placed on the mannequin 5. It is understood that the conventional clean room smock 6 (only a portion of which is shown so that the details of the invention may be identified in the drawings) would cover the entire mannequin 5 body and includes headgear, a mask, gloves, and shoes.

A gas generator 12, under the control of control box 10, is connected to the mannequin 5 and delivers a gas, for example, nitrogen gas ($N_2$) or argon gas (Ar), to the mannequin 5 at a pressure in a range of about 1 to about 5 kg/cm$^3$. A particle generator 14, also under the control of control box 10, is connected to the mannequin 5 and delivers particles to the mannequin 5 having a diameter ranging from about 0.1 to about 5.0 μm. The system can be configured to supply many different-sized particle ranges.

The gas generator 12 is connected via a gas supply line 16 to two gas nozzles 20, one of which is formed in the upper part of the mannequin 5 and the other of which is formed in the lower part of the mannequin 5. A plurality of openings 21 are formed on the surface of each gas nozzle 20. Gas supply valves 26 and 28 respectively connect the gas nozzles 20 to the gas supply line 16, and open or close the flow of gas from the gas generator 12 to the gas nozzles 20.

A plurality of particle outlets 22 are placed at many sites along the mannequin 5, such as head, eyes, nose, ears, mouth, neck, chest, elbows, wrists, hands, waist, knees, and ankles, and where a zipper of the clean room smock is located. The particle outlets 22 are connected to the particle generator 14 through a particle supply line 18. The particle supply line 18 comprises a central supply line with a plurality of branches so as to reach all parts of the mannequin 5. A particle supply valve 30 is installed at each particle outlet 22 and is connected to the particle supply line 18 for opening or closing the flow of particles from the particle generator 14 to the particle outlets 22.

The operation of the particle analyzing system for the clean room smock and a method of analyzing particles according to the present invention will now be described. The above analysis is preferably carried out inside a clean room or chamber having a very high degree of cleanliness.

Referring to FIG. 2, the clean room smock to be analyzed is first cleaned (S40) to remove any particles that are present. Next, a first baseline particle measurement is performed (S42), using a Tumbler tester or Helmkedram tester for example, in order to determine the amount of the particles remaining on the clean room smock after the above cleaning step. Then, the clean room smock is placed on the mannequin 5 having the particle analyzing system of FIG. 1 incorporated therein (S44).

Gas and particles are thereafter supplied to the mannequin 5 and clean room smock (S46). First the gas supply valves 26, 28, connecting the gas nozzles 20 to the gas supply line 16, are selectively opened or closed to provide gas to the upper part and/or the lower part of the mannequin 5. Then, the particle supply valves 30, connecting each of the particle outlets 22 to the particle supply line 18, are selectively opened or closed to provide particles to the sites on the mannequin 5 as described and shown in FIG. 1.

Any number of options exist for supplying the particles to the sites of the mannequin 5 and clean room smock. For example, to isolate the head area, the particle supply valves 30 connected to the particle outlets 22 on the head, eyes, nose, ears, and mouth of the mannequin 5 would be opened, and the particle supply valves 30 connected to the remaining particle outlets 22 on the mannequin 5 would be closed. To isolate the upper part of the mannequin 5, the particle supply valves 30 connected to the particle outlets 22 on the neck, chest, elbows, wrists, waist, and hands of the mannequin 5 would be opened, and the particle supply valves 30 connected to the remaining particle outlets 22 on the mannequin 5 would be closed. Likewise, to isolate the lower part of the mannequin 5, the particle supply valves 30 connected to the particle outlets 22 on the knees, ankles and zipper of the clean room smock of the mannequin 5 would be opened, and the particle supply valves 30 connected to the remaining particle outlets 22 on the mannequin 5 would be closed. Of course, one of ordinary skill in the art would understand that many different combinations of sites could be selectively opened or closed to isolate certain regions of the mannequin 5 and the clean room smock.

Preferably, the nitrogen gas or argon gas is supplied from the gas generator 12 to the mannequin 5, via the gas supply line 16, at a pressure in a range of about 1 to about 5 kg/cm$^3$. Also, particles having a diameter of about 0.1 to about 5.0 μm are supplied from the particle generator 14 to the mannequin 5 via the particle supply line 18. The particles are then discharged into the clean room smock through any of the plurality of open particle outlets 22 corresponding to the sites on the mannequin 5. Of course, different-sized particles may also be provided to determine a broader range of particle generation.

The gas that is discharged into the clean room smock through the gas nozzles 20 installed at the upper and lower parts of the mannequin 5 applies a certain pressure to the clean room smock . This pressure forces the particles of the clean room smock itself to be discharged into the chamber or clean room, as well as the particles discharged through the plurality of particle outlets 22.

A second particle measurement (S48) is performed outside the clean room smock, and the number of particles having a designated size are measured by a particle counter. Finally, in the analysis step (S50), the number of particles from the first particle measurement is subtracted from the number of particles from the second particle measurement, to ascertain the number of particles that permeate through the clean room smock itself. It is readily apparent that certain portions of the clean room smock may be isolated to ascertain the number of the particles that permeate through that particular portion of the clean room smock, for example at the seams, at the upper part of the smock, or the lower part of the smock, by opening and closing the particle supply valves 30 at designated sites of the particle outlets 22.

Therefore, the present invention provides a method of easily measuring the number of particles that permeate through the clean room smock itself by placing the clean room smock on a mannequin 5, thereby eliminating any particle generation variables attributable to an operator. In addition, since a specified pressure is applied to the clean room smock to generate the particles, the present invention further eliminates any variables relating to the intensity level of the activity of the operator during the test. Further, many different areas of the clean room smock can be analyzed for particle permeation, either collectively or individually, by selectively opening/closing the particle supply valves 30 connected to the particle outlets 22.

While the present invention has been described in detail, it should be understood that various changes, substitutions and alterations can be made hereto without departing from the spirit and scope of the invention as defined by the appended claims.

What is claimed is:

1. A particle analyzing system for a clean room smock, comprising:

a mannequin representing a shape of a human body and having a clean room smock placed thereon;

a gas supply apparatus connected to the mannequin, and operative to discharge a gas from a first set of sites on the mannequin; and a particle supply apparatus connected to the mannequin, and operative to discharge particles from a second set of sites on the mannequin and through the clean room smock for analysis.

2. The particle analyzing system of claim 1, the gas supply apparatus comprising:

a gas generator for discharging the gas at a discharge pressure;

a gas supply line connected to the gas generator; and a plurality of gas nozzles, each connected to the gas supply line and each being positioned at corresponding ones of the first set of sites.

3. The particle analyzing system of claim 2, wherein the gas supply line comprises a branch diverging toward an upper part of the mannequin and a branch diverging toward a lower part of the mannequin.

4. The particle analyzing system of claim 3, further comprising a gas supply valve installed between the gas supply line and each of the gas nozzles.

5. The particle analyzing system of claim 2, further comprising a control box connected to the gas generator.

6. The particle analyzing system of claim 1, the particle supply apparatus comprising:

a particle generator for discharging particles having a certain size;

a particle supply line connected to the particle generator; and a plurality of particle outlets, each connected to the particle supply line and each being positioned at corresponding ones of the second set of sites.

7. The particle analyzing system of claim 6, wherein the particle supply line comprises a plurality of branches, each branch diverging toward a separate part of the mannequin.

8. The particle analyzing system of claim 7, wherein the second set of sites comprises sites corresponding to a head, eyes, a nose, ears, a mouth, a neck, a chest, elbows, wrists, a waist, knees, ankles, and hands of the mannequin, and at a location corresponding to a zipper of the clean room smock.

9. The particle analyzing system of claim 8, further comprising a particle supply valve installed between the particle supply line and each of the particle outlets.

10. The particle analyzing system of claim 6, further comprising a control box connected to the particle generator.

11. The particle analyzing system of claim 6, wherein a diameter of the particles is about 0.1 to about 5.0 $\mu$m.

12. The particle analyzing system of claim 1, wherein the gas is nitrogen or argon.

13. The particle analyzing system of claim 1, wherein a discharge pressure of the gas is maintained within a range of about 1 to about 5 kg/cm$^3$.

14. A method of analyzing particles of a clean room smock, comprising:

cleaning a clean room smock to be analyzed;

applying a pressure to the clean room smock to generate particles remaining on the clean room smock;

measuring a number of particles generated by the clean room smock during said applying;

placing the clean room smock on a mannequin corresponding to a shape of a human body;

supplying a gas under pressure through a gas supply line to a first set of sites on the mannequin;

supplying particles through a particle supply line to a second set of sites on the mannequin; and measuring a number of particles discharged from the clean room smock after said supplying particles.

15. The method of analyzing particles of claim 14, wherein said applying a pressure comprises rotating the clean room smock within a chamber to pressurize the clean room smock.

16. The method of analyzing particles of claim 15, further comprising analyzing the number of particles discharged from the clean room smock with respect to particle diameter.

17. The method of analyzing particles of claim 16, wherein said analyzing comprises comparing the number of particles generated by the clean room smock after said cleaning, with the number of particles discharged from the clean room smock after said supplying particles.

18. The method of analyzing particles of claim 14, wherein during said supplying particles, certain ones of the second set of sites on the mannequin are selectively brought into flow communication with the particle supply line for discharging particles at respective sites.

19. The method of analyzing particles of claim 18, wherein after said supplying particles, a number of particles discharged at the certain ones of the second set of sites is measured.

* * * * *